United States Defensive Publication [19] (H) [11] T103,402

Lau [43] Sep. 6, 1983

[54] ARYLOXY SUBSTITUTED PHOTOGRAPHIC COUPLERS AND PHOTOGRAPHIC ELEMENTS AND PROCESSES EMPLOYING SAME

[76] Inventor: Philip T. S. Lau, Kodak Park Works, Rochester, N.Y. 14650

[21] Appl. No.: 463,425

[22] Filed: Feb. 3, 1983

Related U.S. Application Data

[62] Division of Ser. No. 324,237, Nov. 23, 1981.

[51] Int. Cl.[3] ..... C07C 103/75

[52] U.S. Cl. ..... 564/218; 260/509; 548/373; 548/374; 564/123; 564/173; 564/443

[57] ABSTRACT

Couplers of good reactivity contain an aryloxy coupling-off group having in an ortho position a polarizable carbonyl, sulfonyl or phosphinyl substituent group which is free of photographic dye groups and photographic reagent groups.

8 Claims, No Sheets Drawing,

42 Pages Specification

The file of this unexamined application may be inspected and copies thereof may be purchased (849 O.G. 1221, Apr. 9, 1968).